(12) United States Patent
Tanigakiuchi et al.

(10) Patent No.: US 8,648,195 B2
(45) Date of Patent: Feb. 11, 2014

(54) STABILIZED CRYSTAL OF 2-ETHYL-3,7-DIMETHYL-6-(4-(TRIFLUOROMETHOXY)PHENOXY)-QUINOLINE-4-YL METHYL CARBONATE, PROCESS FOR PRODUCING THE CRYSTAL, AND AGRICULTURAL CHEMICAL COMPOSITION COMPRISING THE CRYSTAL

(75) Inventors: Kouki Tanigakiuchi, Kamisu (JP); Mikio Sekiguchi, Saitama-Ken (JP); Hiroki Hotta, Saitama (JP); Shizuo Shimano, Ageo (JP); Akinori Morikawa, Kamisu (JP); Kazumi Yamamoto, Kamakura (JP); Nozomu Nakanishi, Yokohama (JP); Nobuto Minowa, Yokohama (JP); Takashi Watanabe, Yokohama (JP)

(73) Assignees: Nippon Kayaku Co., Ltd., Tokyo (JP); Meiji Seika Pharma Co., Ltd., Tokyo-To (JP)

( * ) Notice: Subject to any disclaimer, the term of this patent is extended or adjusted under 35 U.S.C. 154(b) by 0 days.

(21) Appl. No.: 13/580,550

(22) PCT Filed: Feb. 22, 2011

(86) PCT No.: PCT/JP2011/053781
§ 371 (c)(1),
(2), (4) Date: Nov. 5, 2012

(87) PCT Pub. No.: WO2011/105349
PCT Pub. Date: Sep. 1, 2011

(65) Prior Publication Data
US 2013/0045989 A1    Feb. 21, 2013

(30) Foreign Application Priority Data

Feb. 23, 2010    (JP) ................................. 2010-037475

(51) Int. Cl.
*C07D 215/38*    (2006.01)
(52) U.S. Cl.
USPC ........................... 546/159; 546/162; 504/247

(58) Field of Classification Search
USPC ................................... 546/159, 162; 504/247
See application file for complete search history.

(56) References Cited

U.S. PATENT DOCUMENTS

| 6,486,195 | B1 | 11/2002 | Cvetovich et al. | |
| 7,880,006 | B2 * | 2/2011 | Yamamoto et al. | 546/159 |
| 8,367,833 | B2 * | 2/2013 | Kato et al. | 546/159 |

FOREIGN PATENT DOCUMENTS

| CN | 101472879 | 7/2009 |
| CN | 101621926 | 1/2010 |
| CN | 101626684 | 1/2010 |
| EP | 1 780 202 | 5/2007 |
| JP | 2005-112738 | 4/2005 |
| WO | 2008/020532 | 2/2008 |
| WO | 2008/093325 | 8/2008 |
| WO | 2008/113447 | 9/2008 |
| WO | 2010/007964 | 1/2010 |

OTHER PUBLICATIONS

International Preliminary Report on Patentability and Written Opinion issued Sep. 18, 2012 in International (PCT) Application No. PCT/JP2011/053781.
Supplementary European Search Report issued Jun. 28, 2013 in corresponding European Application No. 11 74 7310.
Office Action issued Jun. 19, 2013 in corresponding Chinese Application No. 201180020111.3, with English translation.
International Search Report issued Mar. 29, 2011 in International (PCT) Application No. PCT/JP2011/053781, of which the present application is the national stage.

* cited by examiner

*Primary Examiner* — D M Seaman
(74) *Attorney, Agent, or Firm* — Wenderoth, Lind & Ponack, L.L.P.

(57) ABSTRACT

An objective of the present invention is to provide a crystal of 2-ethyl-3,7-dimethyl-6-(4-(trifluoromethoxy)phenoxy) quinoline-4-yl methyl carbonate having stable physicochemical properties. The objective is attained by a crystal of 2-ethyl-3,7-dimethyl-6-(4-(trifluoromethoxy)phenoxy) quinoline-4-yl methyl carbonate that exhibits a diffraction peak pattern shown in FIG. 1 as determined by powder X-ray diffractometry.

12 Claims, 8 Drawing Sheets

STABILIZED CRYSTAL OF 2-ETHYL-3,7-DIMETHYL-6-(4-(TRIFLUOROMETHOXY)PHENOXY)-QUINOLINE-4-YL METHYL CARBONATE, PROCESS FOR PRODUCING THE CRYSTAL, AND AGRICULTURAL CHEMICAL COMPOSITION COMPRISING THE CRYSTAL

CROSS-REFERENCE TO RELATED APPLICATIONS

The application is based upon and claims the benefit of priority from the prior Japanese Patent Application No. 37475/2010, filed on Feb. 23, 2010; the entire contents of which are incorporated herein by reference.

TECHNICAL FIELD

The present invention relates to a stabilized crystal of 2-ethyl-3,7-dimethyl-6-(4-(trifluoromethoxy)phenoxy)quinoline-4-yl methyl carbonate having high insecticidal activity and a process for producing the crystal. The present invention also relates to an agricultural chemical composition comprising the stabilized crystal.

BACKGROUND ART

When a certain compound has two or more crystal states, these different crystalline states are called crystal polymorphism. It is generally known that, when crystal polymorphism exists, the transition of crystal form may occur and, further, the crystal polymorphs (crystal forms) in crystal polymorphism are different from each other in stability and physical properties.

The transition of crystal form in the crystal polymorphism is a phenomenon that is frequently found, for example, in drying, grinding, and storage in chemical industry. The transition of the crystal form sometimes leads to serious problems such as consolidation, extension of crystal, powdering, and heat generation. In particular, in the field of agricultural chemicals, the transition of crystal form after formulation sometimes has a significant effect on the properties and quality of agricultural chemicals, for example, efficacy of agricultural chemicals and storage stability of formulations. Highly stable crystal forms have been developed in order to avoid such problems.

For example, patent document 1 describes crystal polymorphism of methazachlor which is an active ingredient for weeding. Specifically, an aqueous suspension composition comprising a crystal polymorph (1A) obtained by crystallization from cyclohexne or toluene causes agglomeration, and, consequently, the composition becomes heterogeneous and not sprayable. On the other hand, an aqueous suspension composition comprising crystal polymorph (1B) obtained by crystallization in the presence of an organic solvent that is miscible with water, polar, and inert does not cause agglomeration and can maintain good properties.

In patent document 2, problems such as consolidation and heat generation caused by the solid-phase transition of polymorphic crystal of Quizalofop-P-ethyl are avoided by obtaining stabilized crystals. Further, in patent documents 3 and 4, the efficacy of thifluzamide which is a fungicidal active ingredient is improved through an improvement in elution of thifluzamide into water by the transition of crystal form of the thifluzamide.

2-Ethyl-3,7-dimethyl-6-(4-(trifluoromethoxy)phenoxy)-quinoline-4-yl methyl carbonate (hereinafter sometimes referred to simply as "compound I") is a compound having a high insecticidal activity (patent documents 5 and 6). Compound I exerts a high insecticidal activity particularly against Lepidoptera, Hemiptera, Coleoptera, Acari, Hymenoptera, Orthoptera, Diptera, and Order Thysanoptera and is expected to be useful as an active ingredient for agricultural and horticultural insecticides. Up to now, any crystal of compound I having high physicochemical stability has not been reported.

PRIOR ART DOCUMENTS

Patent Documents

Patent document 1: Japanese Patent Application Laid-Open No. 66671/1991
Patent document 2: Japanese Patent Application Laid-Open No. 114707/2001
Patent document 3: Japanese Patent Application Laid-Open No. 227538/1997
Patent document 4: Japanese Patent Application Laid-Open No. 1476/1998
Patent document 5: WO 2006/013896
Patent document 6: WO 2010/007964

SUMMARY OF THE INVENTION

Problems to be Solved by the Invention

When an agricultural chemical formulation comprising compound I is prepared in putting compound I having a high insecticidal activity as active ingredient for agricultural chemicals into practical use, an original substance of compound I that can realize the preparation of formulations having high storage stability should be provided. In particular, when compound I is formulated into a dosage form that contains crystals of an active ingredient for agricultural chemicals, for example, dusts, granules, and wettable powders, there is a possibility that the quality of agricultural chemical formulations is lowered by the transition of crystal form during the storage of formulations.

Accordingly, an object of the present invention is to provide a crystal of compound I that does not undergo a change in crystalline properties caused by the transition of crystal form under storage conditions, a process for producing a stabilized crystal of compound I, and an agricultural chemical composition having a high storage stability.

Means for Solving the Problems

The present inventors have found that crystalline compounds I having stable physicochemical properties (hereinafter sometimes referred to simply as "B crystal form") are obtained by dissolving an isolation product of compound I in a solvent and precipitating crystals of compound I at a temperature of 40° C. or above from the solution. The present inventors have also found that agricultural chemical formulations comprising the B crystal form can undergo little deterioration in quality during storage, that is, in consolidation and extension of crystals of compound I and a lowering in efficacy due to the crystal consolidation and extension. The present invention has been made based on such finding.

The present invention will be summarized below.
(1) A crystal of 2-ethyl-3,7-dimethyl-6-(4-(trifluoromethoxy)phenoxy)quinoline-4-yl methyl carbonate that exhibits diffraction peaks at at least the following diffraction angles (2θ) as determined by powder X-ray diffractometry:

| Diffraction angle (2θ) |
| --- |
| 5.3 ± 0.2° |
| 6.9 ± 0.2° |
| 8.5 ± 0.2° |
| 10.0 ± 0.2° |
| 10.3 ± 0.2° |
| 11.3 ± 0.2° |
| 20.3 ± 0.2° |
| 21.0 ± 0.2° |

(2) The crystal of 2-ethyl-3,7-dimethyl-6-(4-(trifluoromethoxy)-phenoxy)quinoline-4-yl methyl carbonate according to (1), which further exhibits diffraction peaks at the following diffraction angles (2θ) as determined by powder X-ray diffractometry:

| Diffraction angle (2θ) |
| --- |
| 12.2 ± 0.2° |
| 16.6 ± 0.2° |
| 17.1 ± 0.2° |
| 18.4 ± 0.2° |
| 22.5 ± 0.2° |

(3) A process for producing the crystal according to (1) or (2), the process comprising precipitating crystals from an alkanol solution of 2-ethyl-3,7-dimethyl-6-(4-(trifluoromethoxy)phenoxy)quinoline-4-yl methyl carbonate at a temperature of 40° C. or above.

(4) A process for producing the crystal according to (1) or (2), the process comprising adding water to an alkanol solution of 2-ethyl-3,7-dimethyl-6-(4-(trifluoromethoxy)phenoxy)quinoline-4-yl methyl carbonate and precipitating crystals therefrom at a temperature of 40° C. or above.

(5) An agricultural chemical composition comprising the crystal according to (1) or (2) as an active ingredient.

(6) The agricultural chemical composition according to (5), further comprising a surfactant and water.

(7) The agricultural chemical composition according to (5), further comprising a surfactant and a solid carrier.

The crystal according to the present invention has high physicochemical stability and can avoid phenomena such as crystal extension, consolidation, and agglomeration of compound I under storage conditions in a crystal state. Accordingly, the present invention can advantageously provide agricultural chemical formulations of compound I that can avoid a crystal form transition phenomenon of an active ingredient and are highly stable in formulation properties in a stored state and insecticidal activity.

DETAILED DESCRIPTION OF THE INVENTION

Figure 1:
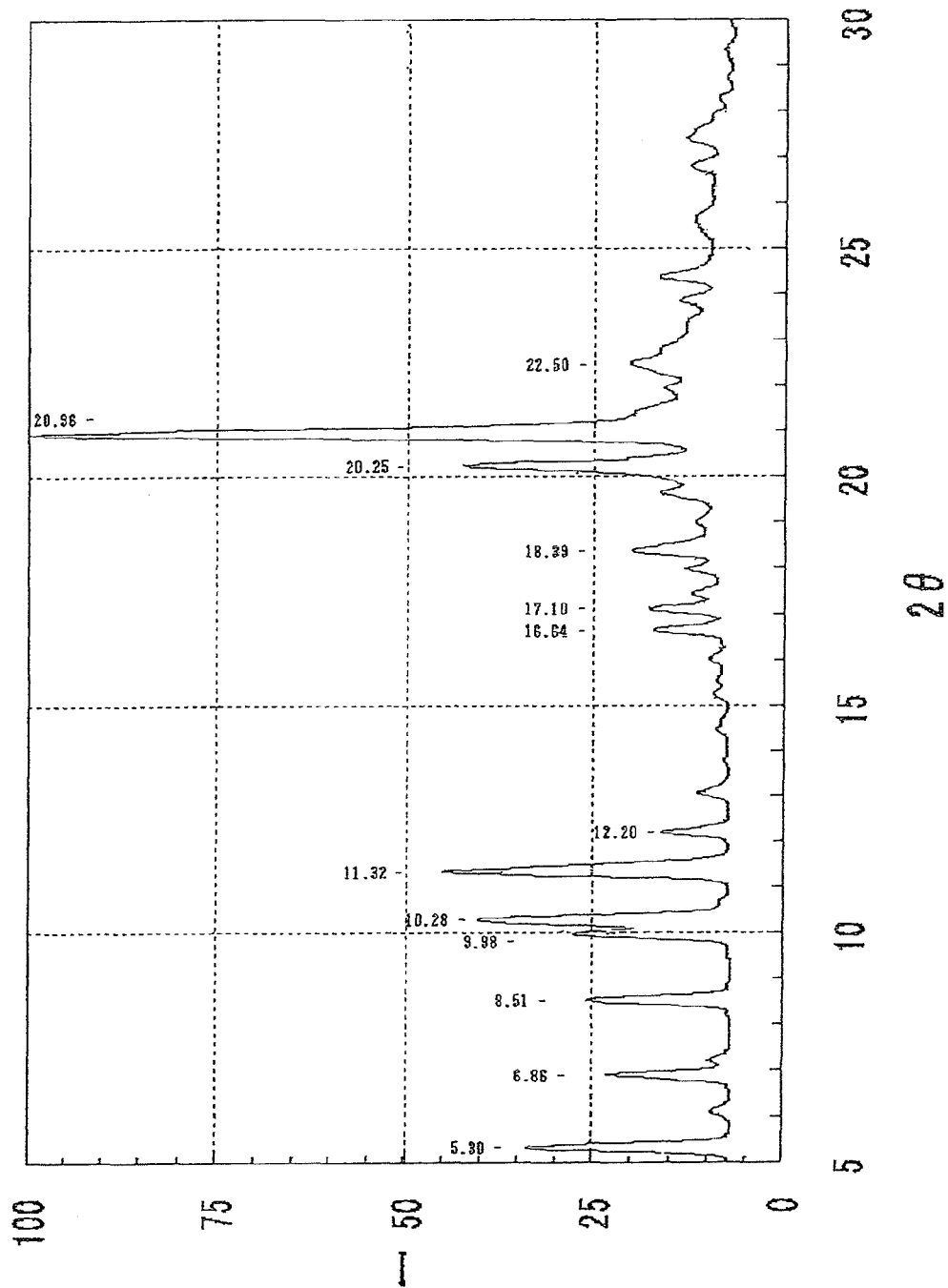
FIG. 1 is a powder X-ray diffraction diagram of B crystal form of compound I.

The crystal (B crystal form of compound I) according to the present invention is characterized by exhibiting a diffraction peak pattern shown in FIG. 1 as determined by powder X-ray diffractometry. That is, the B crystal form of compound I exhibits peaks at 2θ=5.3°, 6.9°, 8.5°, 10.0°, 10.3°, 11.3°, 20.3°, and 21.0° with a relative intensity of not less than 15% as determined by presuming the peak intensity at 2θ=21.0° to be 100. The B crystal form of compound I further exhibits peaks at 2θ=5.3°, 6.9°, 8.5°, 10.0°, 10.3°, 11.3°, 12.2°, 16.6°, 17.1°, 18.4°, 20.3°, 21.0°, and 22.5° with a relative intensity of not less than 10% as determined by presuming the peak intensity at 2θ=21.0° to be 100. The diffraction peak obtained by the powder X-ray diffractometry includes an error range of ±0.2° attributable to measuring apparatuses, analysis environments and other reasons.

Figure 2:
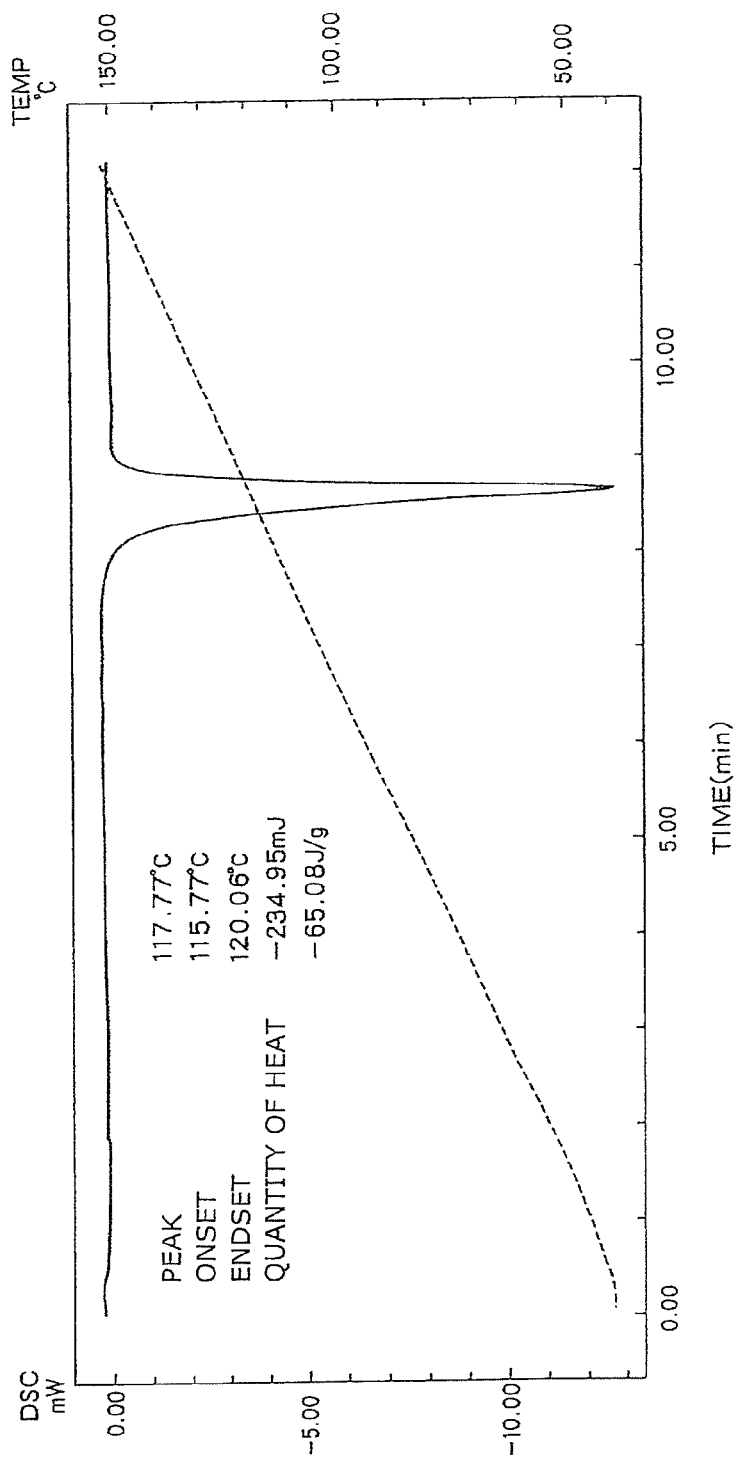
FIG. 2 is an analytical chart of differential scanning calorimetry (DSC) of B crystal form of compound I.

Further, the B crystal form of compound I is characterized by exhibiting an analytical chart shown in FIG. 2 as determined by differential scanning calorimetry (DSC). That is, the B crystal form of compound I is characterized by exhibiting an endothermic peak at around 117.8° C. and exhibiting no other endothermic peak.

On the other hand, WO 2006/013896 discloses compound I but does not describe the crystallinity of the isolation product, and, thus, the properties of the crystal have not hitherto been clarified. The isolation product of compound I obtained by a process described in the prior art document was analyzed for crystallinity. As a result, it was found that a diffraction pattern shown in FIG. 3 was obtained by powder X-ray diffractometry. An isolated crystal of compound I obtained according to WO 2006/013896 (hereinafter referred to simply as "A crystal form") when analyzed by powder X-ray diffractometry exhibited peaks at 2θ=6.9°, 10.4°, 19.1°, 23.5°, 24.3°, 25.0°, and 25.5° with a relative intensity of not less than 15% as determined by presuming the peak intensity at 2θ=19.1° to be 100. Further, the A crystal form of compound I exhibited peaks 2θ=6.9°, 10.4°, 13.1°, 19.1°, 20.9°, 23.5°, 24.3°, 25.0°, and 25.5° with a relative intensity of not less than 10% as determined by presuming the peak intensity at 2θ=19.1° to be 100. The diffraction peak obtained by the powder X-ray diffractometry includes an error range of approximately ±0.2° attributable to measuring apparatuses, analysis environments and other reasons.

Figure 4:
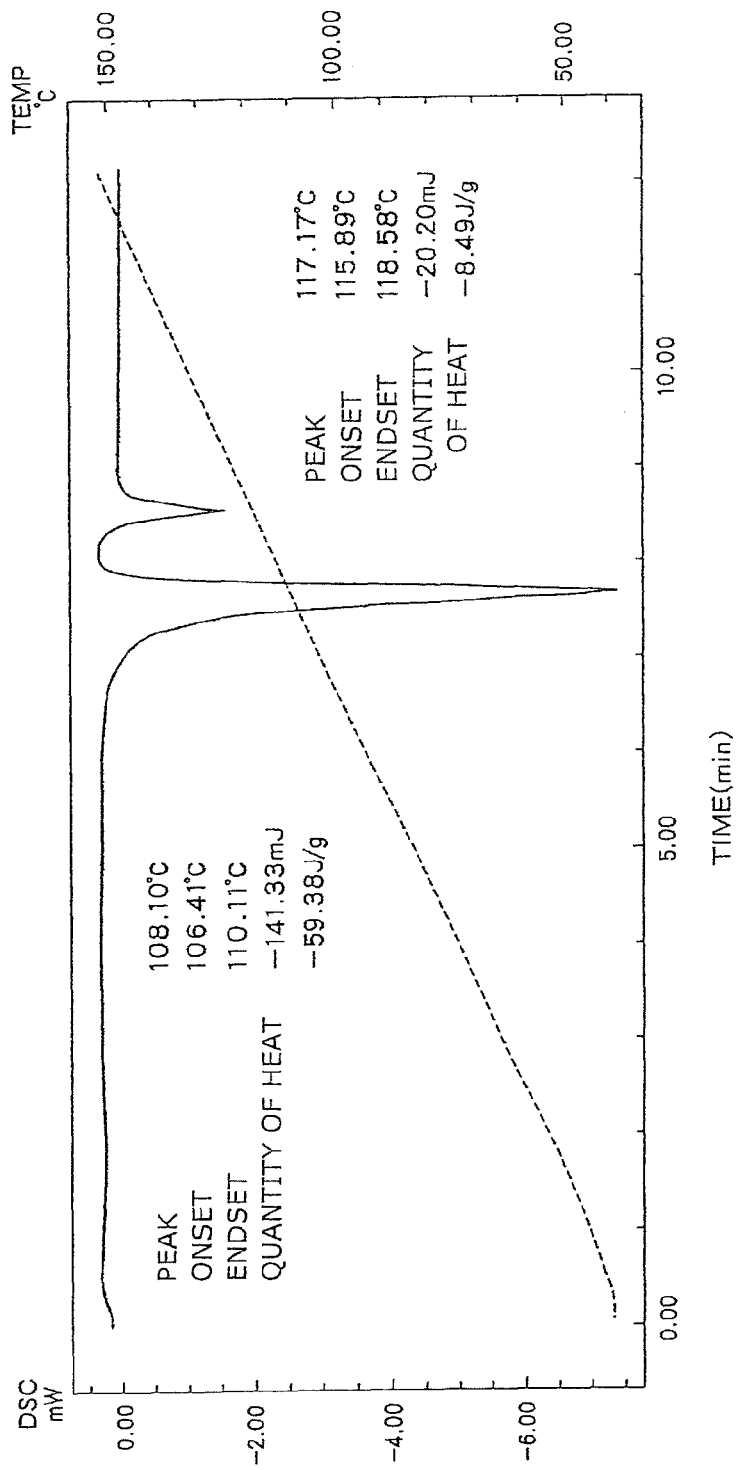
FIG. 4 is an analytical chart of differential scanning calorimetry (DSC) of A crystal form of compound I.

The A crystal form of compound I is characterized by exhibiting an analytical chart shown in FIG. 4 as determined by differential scanning calorimetry (DSC). That is, the A crystal form of compound I exhibited an endothermic peak at around 108.1° C. and further at around 117.2° C.

B crystal form of compound I according to the present invention and the A crystal form described in WO 2006/013896 are different from each other in a diffraction peak pattern as determined by powder X-ray diffractometry and in an endothermic peak pattern as determined by differential scanning calorimetry (DSC).

The results of measurement by powder X-ray diffractometry for the B crystal form and the A crystal form of compound I are those obtained by analyses under the following measurement conditions.

X-ray diffraction data of B crystal form were obtained by measurement with an imaging plate-type X-ray diffraction apparatus (R-AXIS VII manufactured by Rigaku Industrial Corporation) using a Cu-Kα radiation (50 kV, 100 mA, λ=1.5418 angstroms). Specifically, the sample was packed into a glass capillary with an inner diameter of 0.7 mm, and six in total of diffraction images were taken under conditions of a camera length of 300 mm, oscillation 30-degrees spacing, and an exposure time of 45 min to collect data.

X-ray diffraction data of A crystal form were obtained by measurement with an imaging plate-type X-ray diffraction apparatus (R-AXIS VII manufactured by Rigaku Industrial Corporation) using a Cu-Kα radiation (50 kV, 100 mA, λ=1.5418 angstroms). Specifically, the sample was packed into a glass capillary with an inner diameter of 0.7 mm, and six in total of diffraction images were taken under conditions of a camera length of 300 mm, oscillation 45-degrees spacing, and an exposure time of 90 min to collect data.

Contour integration of diffraction images was performed with R-AXIS Display software (Rigaku) (integration range: 45 to 135 degrees). The relative intensity of the integrated intensities was calculated by presuming the maximum integrated intensity to be 100 and was plotted against diffraction angle 2θ to prepare a diffraction pattern.

The crystal according to the present invention (B crystal form of compound I) can be prepared by precipitating crystals of compound I from a solution of compound I while keeping the temperature at 40° C. or above. Specifically, B crystal form of compound I according to the present invention can be prepared by adding a first solvent which is a suitable soluble solvent to compound I, heating the mixture to prepare a compound I solution, adding a second solvent to the heated solution, and precipitating crystals while keeping the temperature within a crystallization tank at 40° C. or above.

The B crystal form of compound I can be specifically prepared as follows. That is, compound I is dissolved in a first solvent, and the solution is heated to prepare a heated compound I solution. Alternatively, a method may also be adopted in which a first solvent is added, the mixture is heated for dissolution to prepare a heated compound I solution. B crystal form can be produced by optionally admixing the heated compound I solution with the first solvent, adding and mixing a second solvent in which the solubility of compound I is lower than the solubility in the first solvent, and precipitating crystals. In order to selectively precipitate the B crystal form, preferably, a process of precipitating crystals of compound I is carried out under heated conditions. The heating temperature may be set to a temperature above room temperature. More preferably, the crystallization process is kept at a temperature of 40° C. or above. Still more preferably, the crystallization process is regulated at a temperature of 45° C. or above. In order to closely regulate the temperature in the crystallization step, preferably, in adding the second solvent to the compound I solution, the inside of the crystallization system is previously thoroughly stirred. The speed of addition of the second solvent to the compound I solution, the temperature of the solvent, the amount of the solvent, and the speed of stirring and the like are not particularly limited as long as desired crystallization can be carried out.

Regarding the heating referred to herein, the upper temperature may be the boiling point of the first solvent. In the preparaiton of the heated compound I solution in this preparation method, preferably, the compound I is in a dissolved state under reflux with heating. Methods for regulating the temperature in the crystallization process include a method in which a second solvent is added to a compound I solution preheated to 40° C. or above with stirring and the inside of a crystallization tank is kept at a temperature of 40° C. or above utilizing the ambient temperature without heating and a method in which a second solvent is added while continuously heating the inside of a precipitation tank, or a method in which a second solvent preheated to 40° C. or above is added to a compound I solution preheated to 40° C. or above. In the crystallization process, the heating step is not particularly limited as long as the temperature is regulated at a temperature of 40° C. or above.

The compound I solution prepared by compound I and a first solvent can be preheated at 40° C. or above. Preferably, the solution is in a completely dissolved state under reflux with the first solvent while heating. More preferably, the solution is a highly concentrated solution of compound I under reflux while heating. Particularly preferably, the solution is a compound I solution that has a concentration regulated close to the saturation solubility under reflux while heating. For example, the heated solution can be prepared by a step of adding, to compound I, a solvent in an amount of 1 to 5 times by volume, preferably 1 to 2 times by volume, the minimum amount that can completely dissolve compound I at the boiling point of the first solvent, and stirring the mixture with heating to dissolve compound I. The second solvent in an amount of 0.1 to 10 times by volume, preferably 0.3 to 3 times by volume, the amount of the first solvent may be added to the heated solution of compound I for crystallization. In this case, in the crystallization process, B crystal form of compound I can be selectively precipitated by regulating the temperature within the crystallization tank at a temperature of 40° C. or above.

Further, the growth of crystals can be promoted without a change in crystal form from the B crystal form by continuing stirring after the precipitation of the B crystal form while heating the crystallization suspension for a few hours. The B crystal form obtained through the step of stirring the crystallization suspension with heating is highly filterable and has a high bulk density and thus is not bulky, leading to an advantageous of excellent handleability.

The B crystal form of compound I according to the present invention can be obtained by filtering the B crystal form suspension of compound I thus obtained to collect wet crystals and drying the wet crystals. The physicochemical stability of the B crystal form of compound I is so high that conditions for the drying step after the collection of crystals are not particularly limited and any drying step and drying conditions may be adopted. Specifically, a heat drying method, a vacuum drying method, or a heat vacuum drying method can be applied.

The first solvent used in the present invention is not particularly limited as long as the solvent is inert to compound I and can dissolve compound I. The solvents that can dissolve compound I may be one of or a mixed solvents composed of two or more of alcohols, ketones, ethers, acetals, esters, nitriles, N-alkylpyrrolidone, N,N-dimethylformamide, N,N-dimethylacetamide, dimethylsulfoxide, aromatic hydrocarbons, and halogenated hydrocarbons. In the solvent that can dissolve compound I, alcohols may be mentioned as preferred solvents as the first solvent for obtaining the B crystal form of compound I according to the present invention when the solubility of compound I, the operation of crystallization step, and the operation of isolation step are taken into consideration. The use of alkanols, that is, acyclic saturated hydrocarbon groups on which one or more hydroxyl groups have been substituted, are more preferred. Alkanols include methanol, ethanol, 1-propanol, isopropyl alcohol, butanol, ethylene glycol, 1,3-butanediol, 1,4-butanediol, glycerin, propylene glycol, ethylene glycol diglycidyl ether, ethylene glycol monomethyl ether, ethylene glycol monoethyl ether, glycerin 1,3-dimethyl ether, diethylene glycol, diethylene glycol monoethyl ether, dipropylene glycol monomethyl ether, and 1,5-pentanediol. Particularly preferred solvents include methanol, ethanol, 1-propanol, and isopropyl alcohol. One of or a mixed solvent composed of two or more of them may be used.

The amount of the first solvent used may be properly set. The solution of compound I in the first solvent is preferably a highly concentrated solution from the viewpoint of the operation of the crystal precipitation step and is more preferably a saturated solution of compound I. Further, the amount of the first solvent is more preferably one that can allow a saturated solution of compound I to be prepared at the boiling point of the first solvent, and is still more preferably one that can allow compound I to be completely dissolved under reflux while heating. Specifically, the amount of the first solvent used is 1 to 20 times by weight the amount of compound I.

Solvents suitable as the second solvent that promotes crystallization in the present invention are not particularly limited as long as they are inert to compound I, dissolve compound I in low solubility, and are miscible with the first solvent at any ratio. Accordingly, a suitable second solvent should be selected based on a relationship of compatibility between the first solvent and the second solvent. When an alkanol which is preferable as the first solvent is applied, a suitable second solvent is water. Water may be purified water or a salt-containing water that contains a suitable inorganic salt or an organic salt. Salts include sodium chloride, potassium chloride, calcium chloride, magnesium chloride, ammonium chloride, sodium carbonate, potassium carbonate, sodium sulfate, magnesium sulfate, sodium phosphate, and potassium phosphate. These salts are used on a condition that they are inert to compound I and mixing of the first solvent with the second solvent gives no salt.

The second solvent may be added in an amount large enough to precipitate crystals of compound I from the compound I solution. For example, the second solvent may be used in an amount of 0.1 to 10 times by volume, preferably 0.3 to 3 times by volume, the amount of the first solvent.

The A crystal form of compound I may be synthesized and isolated according to a method for synthesizing quinoline derivatives described in a pamphlet of International Publication WO2006/013896. The A crystal form of compound I can be selectively prepared by dissolving A crystal form of compound I, which has been isolated by a reaction for synthesizing compound I, in dimethylacetamide solvent at room temperature, pouring the solution of compound I into water kept at a temperature equal to or below room temperature, for example, ice water to precipitate crystals of compound I, and filtering the solution to isolate the crystals.

The B crystal form of compound I in the present invention has a high physicochemical stability and does not cause unfavorable phenomena such as extension of crystals, consolidation, and agglomeration under storage conditions in a crystal state. Accordingly, agricultural chemical compositions comprising B crystal form of compound I as an active ingredient are free from a crystal form transition phenomenon of an active ingredient and thus possess high stability of properties as formulations and high retention of insecticidal activity in a stored state. The form of formulations of agricultural chemical compositions comprising the B crystal form of compound I as an active ingredient is not particularly limited. In a formulation form in which the crystal of the active ingredient is maintained in the formulation, the formulation exerts an advantageous formulation effect by virtue of physicochemical properties of the B crystal form of compound I. Accordingly, this form is preferred. Suitable formulation forms include dusts, wettable powders, granular water-dispersible powders subtle granules, and aqueous suspensions. These forms may be formulated by respective general methods. Any additives other than the B crystal form of compound I added to the agricultural chemical composition according to the present invention may be used without particular limitation as long as the stability of compound I is not sacrificed, and solid carriers, surfactants, and other adjuvants may be used depending upon the formulation form.

For example, the B crystal form of compound I may be mixed with solid carriers and optionally other additives and formulated into dusts, wettable powders, granular water-dispersible powder and subtle granules by conventional methods. Further, the B crystal form of compound I may be mixed with a surfactant and a solvent (for example, water) and optionally other additives and formulated into aqueous suspensions by conventional methods.

Solid carriers usable herein include, for example, talc, bentonite, clay, kaolin, diatomaceous earth, vermiculite, white carbon, calcium carbonate, acid clay, silica sand, silica stone, zeolite, attapulgite, pumice, ammonium sulfate, sodium sulfate, urea, potassium chloride, sodium chloride, crystalline cellulose, carboxymethylcellulose, and xanthan gum.

Nonionic and/or anionic surfactants are applicable as the surfactant. Nonionic surfactants usable in the present invention include polyoxyethylene alkyl ethers, polyoxyethylene styrylphenyl ethers, polyoxyethylene alkyl esters, polyoxyethylene phenyl ether polymers, polyoxyethylene alkylene-arylphenyl ethers, polyoxyethylene polyoxypropylene block polymers, polyoxyethylenated castor oils, polyoxyethylenated hydrogenated castor oils, glyceryl monostearates, and glyceryl distearates. Anionic surfactants include polyoxyethylene styrylphenyl ether sulfate, lignine sulfonates, alkylaryl sulfonates, alkyl naphthalene sulfonates, polycarboxylates, polyoxyethylene polystyryiphenyl ether sulfates and phosphates. Nonionic and anionic surfactants are not limited tehreto as long as the stability of the active ingredient of the agricultural ingredient is not sacrificed. In the present invention, one of or a combination of two or more surfactants selected from the group consisting of these nonionic and anionic surfactants may be used.

Other adjuvants for preparations include anti-settling additives and antifreezing agents. Anti-settling additives include, but are not limited to, bentonite, smectite, xanthan gum, crystalline cellulose, and carboxymethylcellulose. One of or a combination of two or more of them may be used.

Antifreezing agents include, but are not limited to, ethylene glycol, propylene glycol, glycerin, diethylene glycol, and polyethylene glycol. One of or a combination of two or more of them may be used.

The agricultural chemical composition according to the present invention may be used as a mixture or in a combination with, for example, other insecticides, fungicides, miticides, herbicides, plant growth-regulating agents, or fertilizers. Agents which may be mixed or used in combination include those described, for example, in The Pesticide Manual, 13th edition, published by The British Crop Protection Council and SHIBUYA INDEX, the 14th edition, 2009, published by SHIBUYA INDEX RESEARCH GROUP.

More specifically, examples of insecticides include organic phosphoric ester compounds such as acephate, diclorvos, EPN, fenitorothion, fenamifos, prothiofos, profenofos, pyraclofos, chlorpyrifos-methyl, and diazinon; carbamate compounds such as methomyl, thiodicarb, aldicarb, oxamyl, propoxur, carbaryl, fenobucarb, ethiofencarb, fenothiocarb, pirimicarb, carbofuran, and benfuracarb; nereistoxin derivatives such as cartap and thiocyclam; organochlorine compounds such as dicofol and tetradifon; pyrethroid cornpunds such as permethrin, tefluthrin, cypermethrin, deltamethrin, cyhalothrin, fenvalerate, fluvalinate, ethofenprox, and silafluofen; benzoylurea compounds such as diflubenzuron, teflubenzuron, flufenoxuron, and chlorfluazuron; and juvenile hormone-like compounds such as methoprene. Other insecticides include compounds such as buprofezin, hexythiazox, chiordimeform, pyridaben, amitraz, fenpyroxymate, pyrimidifen, tebufenpyrad, fluacrypyrim, acequinocyl, fipronyl, ethoxazole, imidacloprid, chlothianidin, pymetrozine, bifenazate, spirodiclofen, chlorfenapyr, pyriproxyfen, indoxacarb, pyridalyl, or spinosad, avermectin, milbemycin, organometal compouns, and dinitro compounds. Further, the agricultural and horticultural insecticides according to the present invention may also be used as a mixture or in a combination with microbial pesticides such as BT formulations and insect pathological viral agents.

Fungicides usable herein include, for example, strobilrin compounds such as azoxystrobin, kresoxim-methyl, and trifloxystrobin; anilinopyrimidine compounds such as mepanipyrim, pyrimethanil, and cyprodinil; azole compounds such as triadimefon, bitertanol, triflumizole, etaconazole, propiconazole, penconazole, flusilazole, myclobutanil, cyproconazole, tebuconazole, hexaconazole, prochloraz, and simeconazole; quinoxaline compounds such as quinomethionate; dithiocarbamate compounds such as maneb, zineb, mancozeb, polycarbamate, and propineb; phenylcarbamate compounds such as diethofencarb; organochlorine compounds such as chlorothalonil and quintozene; benzimidazole compounds such as benomyl, thiophanate-methyl, and carbendazole; phenylamide compounds such as metalaxyl, oxadixyl, ofurase, benalaxyl, furalaxyl, and cyprofuram; sulfenic acid compounds such as dichlofluanid; copper compounds such as copper hydroxide and oxyquinoline-copper; isoxazole compounds such as hydroxyisoxazole; organophosphorus compounds such as fosetyl-aluminium and tolciofos-methyl; N-halogenothioalkyl compounds such as captan, captafol, and folpet; dicarboxyimide compounds such as procymidone, iprodione, and vinchlozolin; benzanilide compounds such as flutolanil and mepronil; morpholine compounds such as fenpropimorph and dimethomorph; organotin compounds such as fenthin hydroxide, and fenthin acetate; and cyanopyrrole compounds such as fludioxonil and fenpiclonil. Other fungicides include fthalide, fluazinam, cymoxanil, triforine, pyrifenox, fenarimol, fenpropidin, pencycuron, cyazofamid, iprovalicarb, and benthiavalicarb-isopropyl.

Agricultural chemical compositions comprising B crystal form of compound I obtained according to the present invention are advantageous over agricultural chemical compositions comprising A crystal form in that the storage stability is improved, the elongation of crystals is significantly inhibited, and unfavorable phenomena such as lowered efficacy due to the elongation of crystals and consolidation of the agricultural chemical composition are not observed.

EXAMPLES

The present invention is further illustrated by the following Reference Example, Examples, and Comparative Example, and the effect of the present invention is illustrated by Test Examples. However, it should be noted that the present invention is not limited to these Examples.

Analytical Instrument and Measurement Conditions

Analytical instrument and measurement conditions for powder X-ray diffraction measurement of Reference Example and Example 1 are as follows. X-ray diffraction data on A crystal form were obtained by measurement with an imaging plate-type X-ray diffraction apparatus (R-AXIS VII manufactured by Rigaku Industrial Corporation) using a Cu-Kα radiation (50 kV, 100 mA, λ=1.5418 angstroms). Specifically, a sample was packed into a glass capillary with an inner diameter of 0.7 mm, and 6 diffraction images in total were taken under conditions of a camera length of 300 mm, angle of oscillation 45-degrees spacing, and an exposure time of 90 min to collect data.

X-ray diffraction data on B crystal form were obtained by measurement with an imaging plate-type X-ray diffraction apparatus (R-AXIS VII manufactured by Rigaku Industrial Corporation) using a Cu-Kα radiation (50 kV, 100 mA, λ=1.5418 angstroms). Specifically, a sample was packed in a glass capillary with an inner diameter of 0.7 mm, and 6 diffraction images in total were taken under conditions of a camera length of 300 mm, angle of oscillation 30-degrees spacing, and an exposure time of 45 min to collect data.

Contour integration of diffraction images was performed with R-AXIS Display software (Rigaku) (integration range: 45 to 135 degrees). The relative intensity of the integrated intensities was calculated by presuming the maximum integrated intensity to be 100 and was plotted against diffraction angle 2θ to prepare a diffraction pattern.

Reference Example

Preparation of A Crystal Form of Compound I

Dimethylformamide (980 mL) and 98 g of 2-ethyl-3,7-dimethyl-6-(4-(trifluoromethoxy)phenoxy)quinolin-4(1H)-one synthesized according to a process described in WO 2006/013896 were charged under a nitrogen atmosphere into a glass flask (volume: 2000 mL) equipped with a stirrer, a thermometer, a reflux condenser, and a calcium chloride tube, and the mixture was cooled to 15° C. Sodium hydride (55%, 18.2 g) was added dropwise thereto, and the mixture was allowed to react at room temperature for one hr. Methyl chloroformate (32.1 g) was added dropwise thereto, and the mixture was allowed to react at room temperature for one hr. The reaction mixture was poured into 5 L of ice water in a 10-L plastic container and was stirred at room temperature for 2 hr. The precipitated solid was collected by filtration through a suction filter and was washed with n-hexane and water. The solid was dried under reduced pressure to give 103.3 g (yield 91.4%) of compound (2-ethyl-3,7-dimethyl-6-(4-(trifluoromethoxy)phenoxy)quinoline-4-yl methyl carbonate) (A crystal form). The product thus obtained was identified as compound I from the following spectral data.

$^1$H-NMR (CDCl$_3$) 1.38 (t, 3H), 2.31 (s, 3H), 2.41 (s, 3H), 3.01 (q, 2H), 3.88 (s, 3H), 6.97 (d, 2H), 7.14 (s, 1H), 7.20 (d, 2H), 7.94 (s, 1H)

Figure 3:
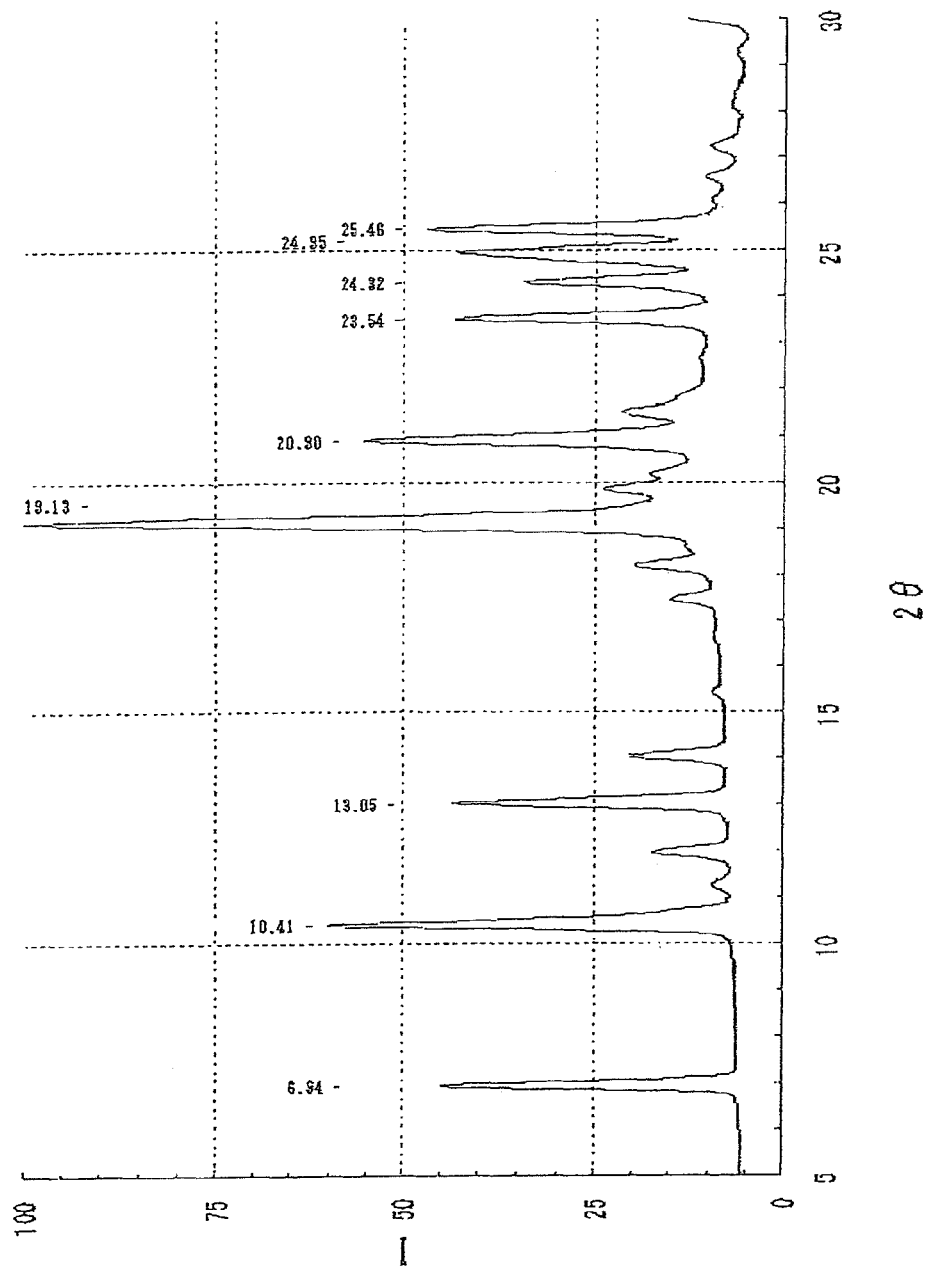
FIG. 3 is a powder X-ray diffraction diagram of A crystal form of compound I.

A diffraction diagram obtained by powder X-ray diffractometry of the compound I (A crystal form) is shown in FIG. 3. The compound I (A crystal form) exhibited peaks at 2θ=6.94°, 10.41°, 19.13°, 23.54°, 24.32°, 24.95°, and 25.46° with a relative intensity of not less than 15% as determined by presuming the peak intensity at 2θ=19.13° to be 100 and exhibited peaks at 2θ=6.94°, 10.41°, 13.05°, 19.13°, 20.90°, 23.54°, 24.32°, 24.95°, and 25.46° with a relative intensity of not less than 10%.

The compound I (A crystal form) was analyzed by differential scanning calorimetry (DSC), and a chart of the obtained results is shown in FIG. 4. The compound I (A crystal form) exhibited endothermic peaks at around 108.1° C. and 117.2° C.

Example 1

Preparation of B Crystal Form of Compound I

The crystal A form of the compound I (148.8 g) obtained in Reference Example and 1200 mL of methanol were added to a 3000-mL four-neck flask equipped with an stirrer, a cooling tube, a dropping funnel, and a thermometer. The mixed solution was heated under reflux to completely dissolve the crystals. Distilled water (520 mL) was added dropwise to the solution in an internal temperature range of 40 to 65° C. for crystallization. The internal temperature of the mixed solution was kept at 40 to 65° C. Further, the suspension was heated under reflux for 2 hr. The suspension was cooled, and crystals were collected by filtration, were washed with 410 mL of a 50% (v/v) aqueous methanol solution, and were dried at 60° C. under reduced pressure to give 140.6 g of B crystal form of compound I. The product thus obtained was identified as compound I from spectral data shown below.

$^1$H-NMR (CDCl$_3$) 1.38 (t, 3H), 2.31 (s, 3H), 2.41 (s, 3H), 3.01 (q, 2H), 3.88 (s, 3H), 6.97 (d, 2H), 7.14 (s, 1H), 7.20 (d, 2H), 7.94 (s, 1H)

A diffraction diagram obtained by powder X-ray diffractometry of the compound I (B crystal form) is shown in FIG. 1. In the powder X-ray diffractometry, the compound I (B crystal form) exhibited peaks at 2θ=5.30°, 6.86°, 8.51°, 9.98°, 10.28°, 11.32°, 20.25°, and 20.96° with a relative intensity of not less than 15% as determined by presuming the peak intensity at 2θ=20.96° to be 100 and exhibited peaks at 2θ=5.30°, 6.86°, 8.51°, 9.98°, 10.28°, 11.32°, 12.20°, 16.64°, 17.10°, 18.39°, 20.25°, 20.96°, and 22.50° with a relative intensity of not less than 10%.

The compound I (B crystal form) was analyzed by differential scanning calorimetry (DSC), and a chart of the obtained results is shown in FIG. 2. The compound I (B crystal form) exhibited an endothermic peak at around 117.8° C. as determined by DSC, and no clear peaks were not observed other than the peak at around 117.8° C.

Example 2

Preparation of Formulation Containing B Crystal Form of Compound I (Aqueous Suspension Formulation)

B crystal form of the compound I (10.8 parts by weight) obtained in Example 1, 1.0 part by weight of Newcalgen FS-3PG (tradename, surfactant, manufactured by Takemoto Oils & Fats Co., Ltd.), 1.0 part by weight of Demol N (tradename, surfactant, manufactured by Kao Corp.), 0.1 part by weight of ANTIFOAM E-20 (tradename, antifoaming agent, manufactured by Kao Corp.), and 30 parts by weight of water were mixed together, and the mixture was ground with a vertical wet grinding mill (1000 rpm, 90 min) manufactured by IMEX Co., Ltd. The ground product was added to a mixture composed of 0.2 part by weight of xanthan gum, 0.3 part by weight of Kunipia F (tradename, thickening agent, manufactured by Kunimine Industries Co., Ltd.), 7.5 parts by weight of propylene glycol, 0.2 part by weight of Proxel GXL(S) (tradename, fungicide, manufactured by Arch Chemicals Japan, Inc.), and 49.1 parts by weight of water to obtain an aqueous suspension formulation (floable formulation) containing 10.8% by weight of B crystal form of compound I.

Example 3

Preparation of Formulation (Wettable Powder) Containing B Crystal Form of Compound I B crystal form of the compound I (10.5 parts by weight) obtained in Example 1, 10.0 parts by weight of Carplex #80 (tradename, white carbon, manufactured by Degussa Japan), 73.5 parts by weight of lactose, 3.0 parts by weight of Newcalgen BX-C (tradename, surfactant, manufactured by Takemoto Oils & Fats Co., Ltd.), and 3.0 parts by weight of Newcalgen WG-4 (tradename, surfactant, manufactured by Takemoto Oils & Fats Co., Ltd.) were mixed together, and the mixture was ground with SampleMill to obtain a wettable powder containing 10.5% by weight of B crystal form of compound I.

Comparative Example 1

Preparation of Formulation Containing A Crystal Form of Compound I (Aqueous Suspension Formulation)

A crystal form of the compound I (10.8 parts by weight), 1.0 part by weight of Newcalgen FS-3PG (tradename, surfactant, manufactured by Takemoto Oils & Fats Co., Ltd.), 1.0 part by weight of Demol N (tradename, surfactant, manufactured by Kao Corp.), 0.1 part by weight of ANTIFOAM E-20 (tradename, antifoaming agent, manufactured by Kao Corp.), and 30 parts by weight of water were mixed together, and the mixture was ground with a vertical wet grinding mill (1000 rpm, 90 min) manufactured by IMEX Co., Ltd. The ground product was added to a mixture composed of 0.2 part by weight of xanthan gum, 0.3 part by weight of Kunipia F (tradename, thickening agent, manufactured by Kunimine Industries Co., Ltd.), 7.5 parts by weight of propylene glycol, 0.2 part by weight of Proxel GXL(S) (tradename, fungicide, manufactured by Arch Chemicals Japan, Inc.), and 49.1 parts by weight of water to obtain an aqueous suspension formulation (floable formulation) containing 10.8% by weight of A crystal form of compound I.

Test Example 1

Storage Test

The aqueous suspension formulations of Example 2 and Comparative Example 1 were stored at 54° C. for 2 weeks, and a change in quality between before and after the storage was observed. The size of crystals before and after the storage test was measured with a laser diffraction particle size distribution measuring apparatus and under an optical microscope.
[Measurement with Laser Diffraction Particle Size Distribution Measuring Apparatus]

Apparatus used: Laser diffraction particle size distribution measuring apparatus SALD-2200 manufactured by Shimadzu Corp The floable formulation diluted with water after the storage test was used for the measurement of particle size with the above measuring apparatus. The A crystal form after the storage could not be suspended in water, and, thus, instead of the suspension, before use in test, was exposed to ultrasonic waves until coarse particle nuclei disappeared.

[Measurement Under Optical Microscope]

Apparatus used: Digital microscope VHX-200 manufactured by Keyence Corp.

Images of the water-diluted floable formulations after the storage test were taken with the apparatus (magnification: 1500 times). The major axes of crystals in the images were measured, and the average was calculated. The A crystal form after the storage could not be suspended in water and, thus, instead of the suspension, before use in test, was exposed to ultrasonic waves until coarse particle nuclei disappeared.

The results of the measurement were as shown in Table 1.

TABLE 1

Results of storage test

Figure 5:
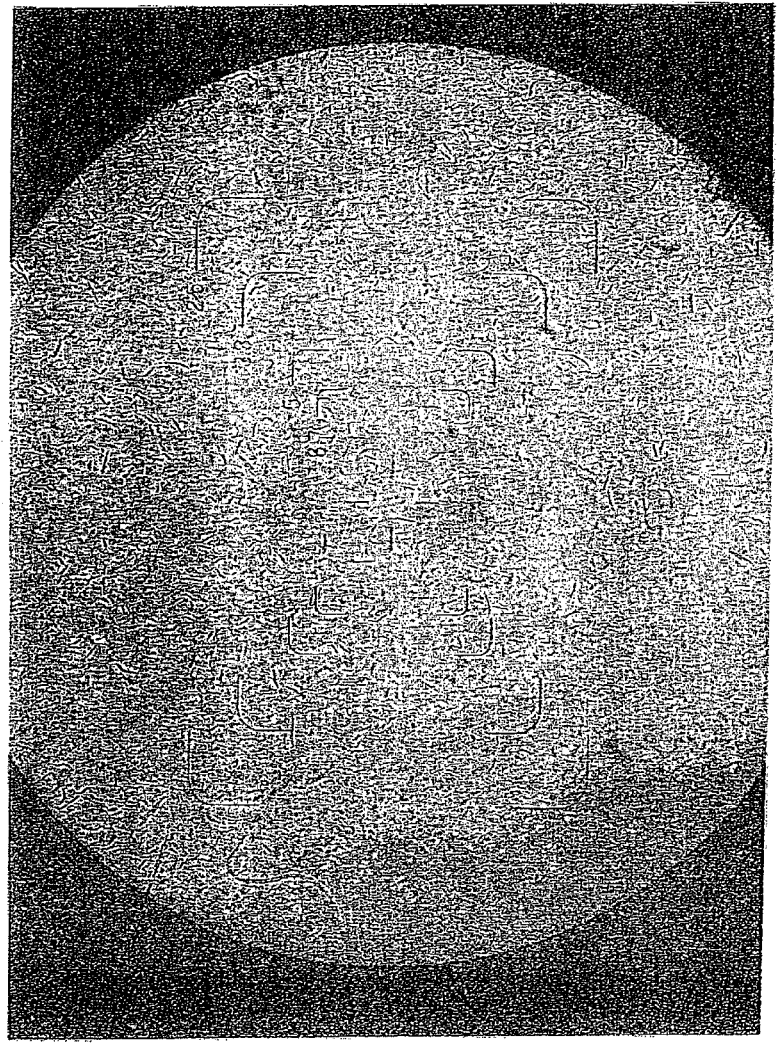
FIG. 5 is a microscopic image photograph (1500 times) of a crystal state of Example 2 (B crystal form) before storage in Test Example 1.
Figure 6:
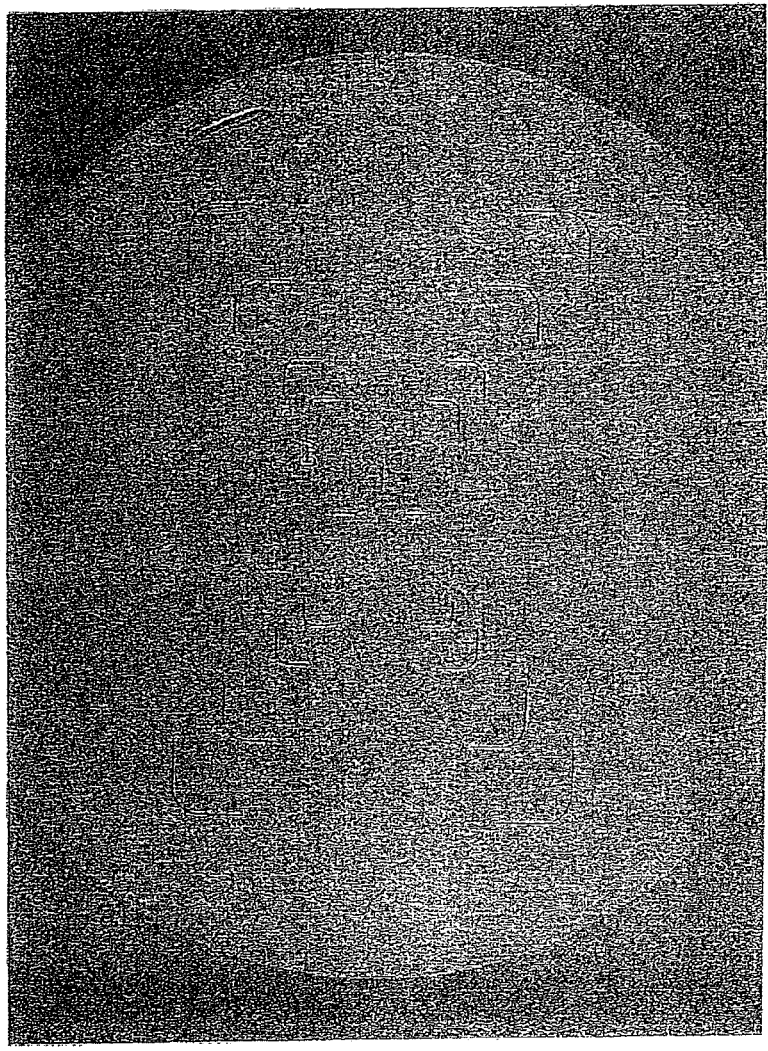
FIG. 6 is a microscopic image photograph (1500 times) of a crystal state of Comparative Example 1 (A crystal form) before storage in Test Example 1.
Figure 7:
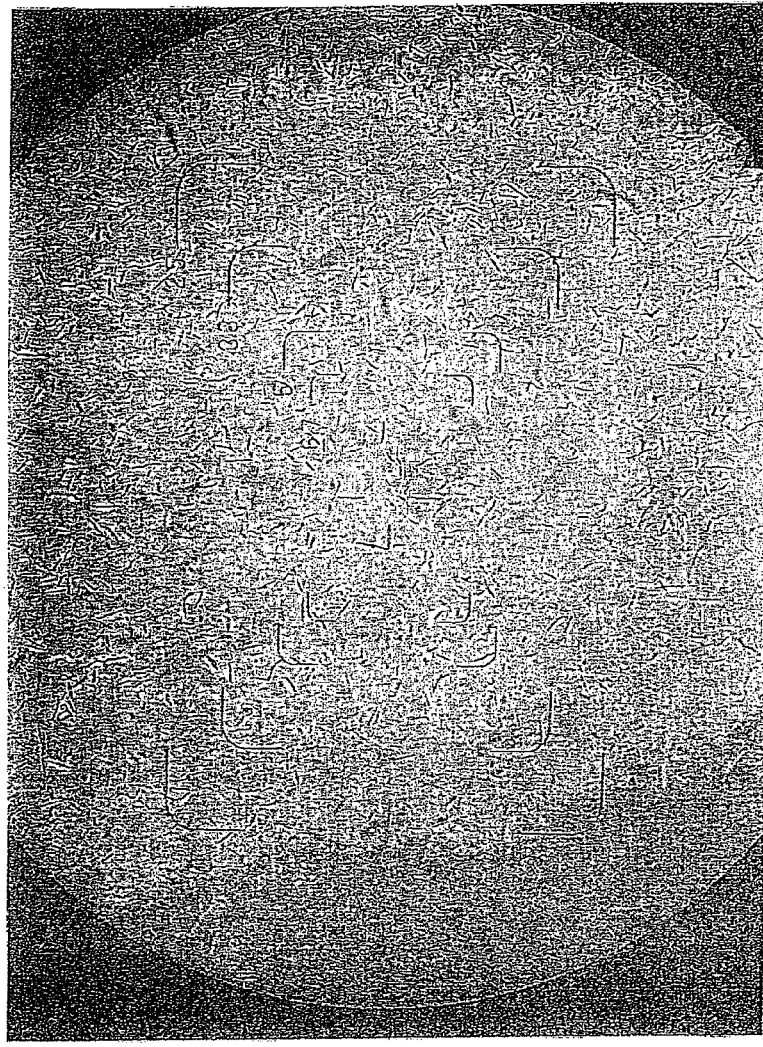
FIG. 7 is a microscopic image photograph (1500 times) of a crystal state of Example 2 (B crystal form) after storage in Test Example 1.
Figure 8:
FIG. 8 is a microscopic image photograph (1500 times) of a crystal state of Comparative Example 1 (A crystal form) after storage in Test Example 1.

| Test sample formulation | Before storage | | | After storage | | |
|---|---|---|---|---|---|---|
| | Particle diameter | Crystal image | Properties | Particle diameter | Crystal image | Properties |
| Example 2 (B crystal form) | X: 1.4 μm Y: 1.7 μm | See FIG. 5 | Viscous liquid | X: 1.4 μm Y: 1.7 μm | See FIG. 7 | Viscous liquid |
| Comparative Example 1 (A crystal form) | X: 1.6 μm Y: 1.6 μm | See FIG. 6 | Viscous liquid | X: 4.1 μm Y: 25 μm | See FIG. 8 | Agglomerated |

X: Results of measurement with laser diffraction particle size distribution measuring apparatus
Y: Results of measurement under optical microscope Aqueous suspension formulations of Example 2 (formulation comprising B crystal form) and Comparative Example 1 (formulation comprising A crystal form) were stored for 2 weeks in a thermostatic chamber of 54° C. As a result, the formulation of Example 2 had properties remaining unchanged and maintained flowability as an aqueous suspension formulation. The particle diameter of the formulation of Example 2 after the storage test remained substantially unchanged from the particle diameter before the storage test, and the microscopic images of particulate state (see FIGS. 5 and 7) show that the growth of the crystal particles was inhibited. On the other hand, the formulation of Comparative Example 1 after the storage test was in an agglomerated state, lost flowability as an aqueous suspension formulation and thus suffered from difficulties in dilution with water, making it difficult to apply the diluted formulation as agricultural and horticultural insecticides. The microscopic images of particulate state (see FIGS. 6 and 8) showed crystal extension involved in the growth of crystal particles during storage, posing a problem of storage stability as aqueous suspension formulations. The particle diameter of the formulation of Comparative Example 1 after the storage test had a clearly increased as compared with the particle diameter before the storage test. The formulation of Comparative Example 1 after the storage test was in an agglomerated state and was not suspended in water. Accordingly, the formulation was treated by ultrasonic irradiation treatment before the measurement. Therefore, it is considered that the actual particle diameter of the formulation of Comparative Example 1 after the storage is larger than the measured value shown in Table 1.

The B crystal form of compound I according to the present invention had high physicochemical stability and possessed high storage stability. Agricultural chemical formulations having high storage stability can be provided by adopting B crystal form of compound I as an original substance of an active pharmaceutical ingredient.

Test Example 2

Efficacy Confirmation Test

The aqueous suspension formulations of Example 2 and Comparative Example 1 were stored at 54° C. for 2 weeks. The aqueous suspension formulations were diluted with water to prepare water-diluted solutions having predetermined concentrations. The diluted solutions (2 mL) were applied to leaf disks of cucumbers. After air drying, 25 to 40 adults of Bemisia tabaci were released. A absorbent cotton lid was put on the container, and the container was placed upside down. After 2 days from the treatment, the number of dead adults was counted to calculate LC50 (ppm). The particle diameter was measured with the laser diffraction particle size distribution measuring apparatus and according to the procedure described in Test Example 1.

The results of the measurement were as shown in Table 2.

TABLE 2

Results of efficacy confirmation test

| | Example 2 (B crystal form) | Comparative Example 1 (A crystal form) |
|---|---|---|
| Average particle diameter before introduction into thermostatic chamber at 54° C. (μm) | 1.9 | 1.6 |
| Average particle diameter after storage at 54° C. for 2 weeks (μm) | 2.1 | 4.1 |
| LC50 exhibited by formulation after storage at 54° C. (ppm) | 1.4 | 5.1 |

For the formulation comprising B crystal form of Example 2, the particle diameter of compound I in the formulation after the storage remained substantially unchanged, whereas, for the formulation comprising A crystal form of Comparative Example 1, an increase in particle diameter caused by the growth of crystals of compound I during storage was observed. In the pediculicidal activity test of both sample formulations against Bemisia tabaci, for Comparative Example 1, a lowering in pediculicidal activity was observed. It is considered that the lowered efficacy is attributable to a reduced probability of contact as a result of a reduction in specific surface area by an increase in particle size of A crystal form during the storage. Accordingly, it was demonstrated that, in the aqueous suspension formulation, a change in crystallized state of compound I which is an active ingredient for insecticidal activity has a significant influence on the insecticidal activity.

As is apparent from the results of Test Examples 1 and 2, when agricultural chemical formulations comprising compound I as an active ingredient of agricultural chemicals are prepared, agricultural chemical formulations that, under long-term storage conditions, are less likely to undergo a change in properties, can maintain a predetermined insecticidal activity, and have high long-term storage stability can be provided by using B crystal form of compound I according to the present invention as an original substance of an active ingredient of agricultural chemicals.

The invention claimed is:

1. A crystal of 2-ethyl-3,7-dimethyl-6-(4-(trifluoromethoxy)phenoxy)quinoline-4-yl methyl carbonate that exhibits diffraction peaks at at least the following diffraction angles (2θ) as determined by powder X-ray diffractometry:

| Diffraction angle (2θ) |
| --- |
| 5.3 ± 0.2° |
| 6.9 ± 0.2° |
| 8.5 ± 0.2° |
| 10.0 ± 0.2° |
| 10.3 ± 0.2° |
| 11.3 ± 0.2° |
| 20.3 ± 0.2° |
| 21.0 ± 0.2°. |

2. The crystal of 2-ethyl-3,7-dimethyl-6-(4-(trifluoromethoxy)phenoxy)quinoline-4-yl methyl carbonate according to claim 1, which further exhibits diffraction peaks at the following diffraction angles (2θ) as determined by powder X-ray diffractometry:

| Diffraction angle (2θ) |
| --- |
| 12.2 ± 0.2° |
| 16.6 ± 0.2° |
| 17.1 ± 0.2° |
| 18.4 ± 0.2° |
| 22.5 ± 0.2°. |

3. A process for producing the crystal according to claim 1, the process comprising precipitating crystals from an alkanol solution of 2-ethyl-3,7-dimethyl-6-(4-(trifluoromethoxy)phenoxy)quinoline-4-yl methyl carbonate at a temperature of 40° C. or above.

4. A process for producing the crystal according to claim 1, the process comprising adding water to an alkanol solution of 2-ethyl-3,7-dimethyl-6-(4-(trifluoromethoxy)phenoxy)quinoline-4-yl methyl carbonate and precipitating crystals therefrom at a temperature of 40° C. or above.

5. An agricultural chemical composition comprising the crystal according to claim 1 as an active ingredient.

6. The agricultural chemical composition according to claim 5, further comprising a surfactant and water.

7. The agricultural chemical composition according to claim 5, further comprising a surfactant and a solid carrier.

8. A process for producing the crystal according to claim 2, the process comprising precipitating crystals from an alkanol solution of 2-ethyl-3,7-dimethyl-6-(4-(trifluoromethoxy)phenoxy)quinoline-4-yl methyl carbonate at a temperature of 40° C. or above.

9. A process for producing the crystal according to claim 2, the process comprising adding water to an alkanol solution of 2-ethyl-3,7-dimethyl-6-(4-(trifluoromethoxy)phenoxy)quinoline-4-yl methyl carbonate and precipitating crystals therefrom at a temperature of 40° C. or above.

10. An agricultural chemical composition comprising the crystal according to claim 2 as an active ingredient.

11. The agricultural chemical composition according to claim 10, further comprising a surfactant and water.

12. The agricultural chemical composition according to claim 10, further comprising a surfactant and a solid carrier.

* * * * *